United States Patent [19]

Uyeo et al.

[11] 4,058,521
[45] Nov. 15, 1977

[54] 2-HALOMETHYL-2-NUCLEOPHILIC SUBSTITUTED METHYL PENICILLINS

[75] Inventors: Shoichiro Uyeo, Toyonaka; Tsutomu Aoki, Sennan; Wataru Nagata, Nishinomiya, all of Japan

[73] Assignee: Shionogi & Co., Ltd., Osaka, Japan

[21] Appl. No.: 762,185

[22] Filed: Jan. 24, 1977

[30] Foreign Application Priority Data

Jan. 23, 1976 Japan .................................. 51-6960

[51] Int. Cl.² .................. C07D 499/44; A61K 31/43
[52] U.S. Cl. ............................. 260/239.1; 260/239 A;
260/302 F; 260/302 SD; 260/308 D; 424/244;
424/246; 424/269; 424/270; 424/271; 544/24;
544/25; 544/26; 544/27; 544/22; 544/28;
544/29; 544/30; 544/16
[58] Field of Search .................................. 260/239.1

[56] References Cited

U.S. PATENT DOCUMENTS

| | | | |
|---|---|---|---|
| 3,275,626 | 9/1966 | Morin et al. | 260/243 C |
| 3,954,732 | 5/1976 | Kamiya et al. | 260/239.1 |
| 3,993,646 | 11/1976 | Kamiya et al. | 260/239.1 |

Primary Examiner—Gerald A. Schwartz
Attorney, Agent, or Firm—Wenderoth, Lind & Ponack

[57] ABSTRACT

Antibacterial compounds of the formula

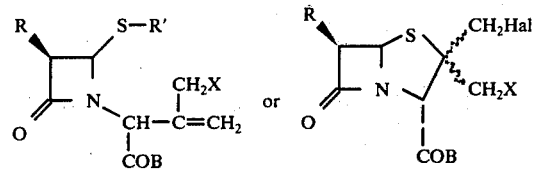

(where
COB is carboxy or protected carboxy;
Hal is halogen;
R is amino or protected amino;
R' is mercapto-protecting group; and
X is nucleophilic group)

are prepared from penicillin 1-oxides having X on its 2-methyl group, and found to be used as starting materials for preparing cephalosporins.

1 Claim, No Drawings

2-HALOMETHYL-2-NUCLEOPHILIC SUBSTITUTED METHYL PENICILLINS

This invention relates to antibacterial azetidinone compounds (I) and (II) represented by the following formula:

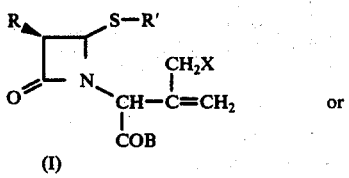

(I)

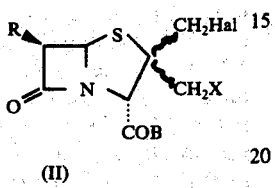

(II)

(where
COB is carboxy or protected carboxy;
Hal is halogen;
R is amino or protected amino;
R' is mercapto-protecting group; and
X is nucleophilic group),
their synthesis, and uses. The compounds are also useful intermediates for synthesizing cephalosporins from penicillins.

In compounds (I) and (II), the protected amino represented by R includes those which constitute side chains of natural or synthetic penicillins or cephalosporins [e.g. acylamino (including diacylamino), hydrocarbylamino (including hydrocarbylideneamino), silylamino, sulfenylamino, etc.].

The acyl of acylamino represented by R can contain up to 25 carbon atoms and includes conventional acyls used in chemistry of penicillins and cephalosporins, and is exemplified by an inorganic acyl including carbonic acyl (e.g. 2-8C alkoxycarbonyl, 8-15C aralkoxycarbonyl, 6-11C aryloxycarbonyl), and organic acyl including 1-5C alkanoyl, 3-8C cycloalkanoyl, 7-20C aralkanoyl, 7-11C aroyl, 1-5C arkylsulfonyl, 6-10C arylsulfonyl, and 1-5C alkylphosphonyl.

These acyls, where possible, may have a hetero atom in the main nucleus, unsaturation, or substituent e.g. a halogen, (e.g. fluorine, chlorine, bromine), nitrogen function (e.g. amino, hydrazo, azido, 1-5C alkylamino, 6-10C arylamino, 1-8C acylamino, 1-5C alkylideneamino, 1-8C acylimino, nitro), oxygen function (e.g. hydroxy, 1-5C alkoxy, 7-20C aralkoxy, 6-10C aryloxy, 1-8C acyloxy, oxo), sufur function (e.g. mercapto, 1-5C alkylthio, 7-9C aralkylthio, 6-10C arylthio, 1-8C acylthio, thioxo, sulfo, sulfonyl, sulfinyl, 1-5C alkoxysulfonyl, 6-10C aryloxysulfonyl, carbon function (e.g. 1-5C alkyl, 1-5C alkenyl, 7-10C aralkyl, 6-10C aryl, carboxy, 2-6C carbalkoxy, carbamoyl, 1-8C alkanoyl, 7-11C aroyl, 1-5C aminoalkyl, 7-10C aralkanoyl, cyano), phosphorus function (e.g. phospho, phosphoroyl) or like substituents.

Representative acyls include following groups:
1. 1-5C alkanoyl;
2. 2-5C haloalkanoyl;
3. azidoacetyl;
4. cyanoacetyl;
5. acyls of the formula:

Ar—CQQ'—CO—

(where
Q and Q' each is hydrogen or methyl; and
Ar is phenyl, dihydrophenyl, or a monocyclic heterocyclic aromatic group containing 1 to 4 hetero atoms selected from nitrogen, oxygen, and/or sulfur atoms, each optionally substituted by e.g. 1-5C alkyl, 1-5C alkoxy, halogen, trifluoromethyl, hydroxy, cyano, aminomethyl, nitroso, and nitro).
6. acyls of the formula:

Ar—G—CQQ'—CO—

(where
G is oxygen or sulfur; and
Ar, Q, and Q' are defined above);
7. acyls of the formula:

Ar—CHT—CO—

(where
Ar is defined above; and
T is
i. amino, ammonio, amino protected by an amino-protecting group (including acyls e.g. benzyloxycarbonyl, 2-8C alkoxycarbonyl, cyclopentyloxycarbonyl, cyclohexyloxycarbonyl, benzyhydryloxycarbonyl, cyclopropylmethoxycarbonyl, methanesulfonylethoxycarbonyl, 2,2,2-trichloroethoxycarbonyl, guanidylcarbonyl, substituted ureidocarbonyl, b 1-5C alkanoyl, pyronecarbonyl, thiopyronecarbonyl, pyridonecarbonyl, and aromatic carbocyclic or heterocyclic acyl optionally substituted by e.g. halogen, trifluoromethyl, 1-5C alkyl, 1-5C aminoalkyl, 1-5C hydroxyalkyl; trityl, and other amino-protecting groups) or protected amino in the form of phthalimino or enamino derived from acetoacetates, acetylacetone, acetoacetonitrile, and like protecting groups;
ii. hydroxy, 1-3C alkoxy, or 1-5C acyloxy;
iii. carboxy, 2-10C alkoxycarbonyl, indanyloxycarbonyl, phenoxycarbonyl, dimethylphenoxycarbonyl, or like groups; or
iv. azido, cyano, carbamoyl, sulfo, 1-3C alkoxysulfonyl, 1-3C alkoxyphosphonyl, or like groups);
8. 3-5C 2-syndon-3-alkanoyl;
9. 6-8C (2- or 4-pyridon-1-yl) alkanoyl;
10. 5-aminoadipoyl, 5-aminoadipoyl protected at the amino or carboxy;
11. acyls of the formula:

L—O—CO—

(where L is an easily removable 1-10C hydrocarbyl e.g. 2,2,2-trichloroethyl, isobornyl, t-butyl, 1-methylcyclohexy, 2-alkoxy-t-butyl, benzyl, p-nitrobenzyl, p-methoxybenzyl, benzyhydryl), and the like acyls.

Typical examples of Ar in the said definition include furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, and dihydrophenyl, each optionally may be substituted by e.g. halogen, 1-5C alkyl, hydroxy, aminomethyl, or 1-3C alkoxy.

Silyl e.g. tri-1–5C-alkylsilyl, and sulfenyl e.g. phenylsulfenyl, o-nitrophenylsulfenyl are conventional aminoprotecting groups.

The hydrocarbyls of said hydrocarbylamino represented by R include easily removable 1–20C aliphatic hydrocarbyls (e.g. 1–5C alkyl, 1–5C alkenyl, 7–20C aralkyl) and monocyclic aryls optionally substituted by halogen, nitrogen-, oxygen-, sulfur-, carbon-, and phosphorus-functions referred to above. These hydrocarbyls can be divalent hydrocarbyls e.g. 1–5C alkylene, 7–15C aralkylene, 1–5C alkylidene, 7–15C aralkylidene, α-halo-or α-1–5C alkoxy-7–15C-aralkylidene, 13–20C diarylmethylidene, 3–10C cycloalkylidene, or other divalent hydrocarbyls. Further, two amino substituents being acyl and hydrocarbyl can be combined to form a ring structure (4-oxo-3-imidazolidinyl ring, etc. ). These groups can also have substituents or unsaturations as cited above.

COB in Compounds (I) and (II) is carboxy or protected carboxy. Representatives of them include those constituting esters [1–5C alkyl (e.g. methyl, ethyl, trichloroethyl, t-butyl esters), 7–20C aralkyl (e.g. benzyl, methoxybenzyl, nitrobenzyl, diphenylmethyl, trityl esters), 6–12C aryl (e.g. phenyl and naphthyl esters), metal (e.g. trimethylthylsilyl, methoxydimethylsilyl, trimethylstannyl esters), and other esters], acid anhydrides, salts (e.g. sodium, potassium, magnesium, aluminum salts), thiol esters, amides, hydrazides, azides, and other derivatives of carboxy groups. COB can, where possible, have substituents referred to above e.g. halogen, sulfur-, oxygen-, nitrogen-, carbon-, or other functions or can be unsaturated.

Among these protected carboxy, important groups for COB are those inert to the reaction and removable after the reaction without adverse effect on the other part of the molecule (e.g. 1–3C haloalkyl, 2–10C acylalkyl, 2–7C alkoxyalkyl, 2–7C acyloxyalkyl, 7–20C aralkyl esters, 2–6C dialkylhydrazides, alkali metal salts, and 1–12C alkylamine salts).

The protecting group in COB has no meaning other than protection and deprotection, and wide variation can be possible without changing the gist of this invention.

X in Compounds (I) and (II) is nucleophilic group. The nucleophilic group can be halogen, acyloxy, hydroxy, mercapto, 1–3C alkylthio, 1–12C arylthio including heteroaromatic thio represented by partial formula:

Ar—S—

(where Ar is defined above) and other nucleophilic groups bound to methyl at position 3 of cephem ring in known cephalosporins. It can be exemplified by halogen (e.g. chlorine, bromine, fluorine), acyloxy (e.g. formyloxy, acetyloxy, propionyloxy, benzoyloxy, sulfonyloxy, carbonic or sulfuric acyloxy), 1–3C alkoxy (e.g. methoxy, ethoxy, butoxy), arylthio (e.g. phenylthio, nitrophenylthio, tolylthio, 1,3,4-thiadiazolylthio, 2-methyl-1,3,4-thiadiazol-5-ylthio, 2-hydroxymethyl-1,3,4-thiadiazol-5-ylthio, 1-methyltetrazol-5-ylthio, 1,2,3-triazol-5-ylthio, pyridazin-3-ylthio, 1-oxidopyridin-2-yl-thio) or like nucleophiles.

When a group COB, R, R', or X is unstable under the reaction condition, it can be protected prior to and deprotected after the reaction to avoid unfavorable side reactions.

Representative R' in Compounds (I) includes those which are eliminated to form penam- or cephem-ring under the reaction conditions, e.g. aliphatic or aromatic thio (1–5C alkylthio, 7–15C aralkylthio, 6–10C arylthio, etc.), and eliminating group (thiocyanato, arylamino, sulfonyl, sulfo, etc.). These mercapto protecting groups can, where possible, possess a substituent e.g. oxygen-, nitrogen-, sulfur-, carbon-, etc. functions or halogen, or can be unsaturated. Further, they may have a hetero atom in the main nucleus. Examples of R' include alkylthio, arylthio (aryl e.g. said Ar), acyl, cyano, thiocyano, sulfo, anilino, and other mercaptoprotecting groups.

Suitable Hal is chlorine or bromine, but iodine and pseudohalogens are also available.

Preferable R is phenylacetamido, phenoxyacetamido, tetrazol-1-ylacetamido, N-acetyl-N-phenylacetylamino, and 2-thienylacetamido. Preferable COB is carboxy, 2,2,2-trichloroethoxycarbonyl, benzyloxycarbonyl, p-nitrobenzyloxycarbonyl, p-methoxybenzyloxycarbonyl, and benzhydryloxycarbonyl. Preferable X is chlorine, acetoxy, 5-methyl-1,3,4-thiadiazol-2-ylthio, or 1-methyltetrazol-5-ylthio. Most preferable R' is benzothiazol-2-ylthio and thiazol-2-ylthio.

Some of specific and preferable examples of Compounds (I) include those having the following groups:

1. COB = benzhydryloxycarbonyl, R = phenoxyacetamido, R' = 2-benzothiazolylthio, and X = acetoxy;
2. COB = 2,2,2-trichloroethoxycarbonyl, R = phenylacetamido, R' = 2-benzothiazolylthio, and X = acetoxy;
3. COB = benzyloxycarbonyl, R = phenoxyacetamido, R' = 2-benzothiazolylthio, and X = acetoxy;
4. COB = benzhydryloxycarbonyl, R = phenoxyacetamido, R' = 2-benzothiazolylthio, and X = chloro;
5. COB = p-methoxybenzyloxycarbonyl, R = 1-tetrazolylacetamido, R' = 2-benzothiazolylthio, and X = chloro;
6. COB = benzhydryloxycarbonyl, R = N-phenylacetyl-N-acetylamino, R' = 2-benzothiazolylthio, and X = acetoxy; or
7. COB = carboxy, R = 2-thienylacetamido, R' = 2-benzothiazolylthio, and X = 5-methyl-1,3,4-thiadiazol-2-ylthio.

Some of specific and preferable examples of Compounds (II) include those having the following groups:

1. COB = benzhydryloxycarbonyl, Hal = bromo, R = phenoxyacetamido, and X = acetoxy;
2. COB = 2,2,2-trichloroethoxycarbonyl, Hal = bromo, R = phenylacetamido, and X = acetoxy;
3. COB = benzyloxycarbonyl, Hal = bromo, R = phenoxyacetamido, and X = acetoxy;
4. COB = benzhydryloxycarbonyl, Hal = bromo, R = phenoxyacetamido, and X = chloro;
5. COB = p-methoxybenzyloxycarbonyl, Hal = bromo, R = 1-tetrazolacetamido, and X = chloro;
6. COB = diphenylmethoxycarbonyl, Hal = bromo, R = N-phenylacetyl N-acetylamino, and X = acetoxy; or
7. COB = diphenylmethoxycarbonyl, Hal = bromo, R = N-phenylacetyl N-acetylamino, and X = chloro, R = 2-thienylacetamide, and X = 5-methyl-b 1,2,4-thiadiazol-2-ylthio.

The starting materials of this invention, Compounds (III) and (IV), are described in e.g. British Pat. No. 1,445,845 and Japanese patent application No. 8994/1976.

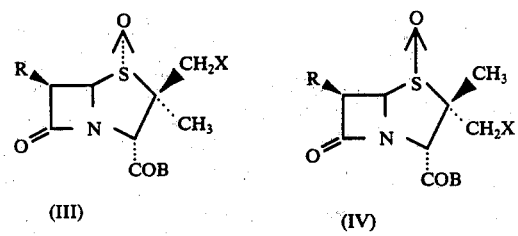

(where COB, R, and X are defined above).

Compounds (I) can be prepared by treatment of Compounds (III) or (IV) with a compound of the formula:

HR'

(where R' is defined above) according to following scheme where COB, R, R', and X are defined above:

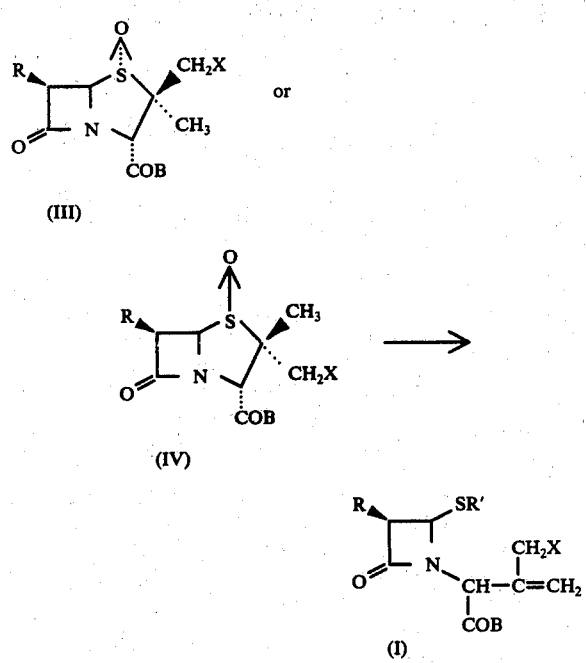

Heating of the starting materials (III) and (IV) at 70° C to 150° C gives the corresponding compounds where S-oxide and 2-CH₂X groups are simultaneously reversed, namely by an inversion of the following scheme:

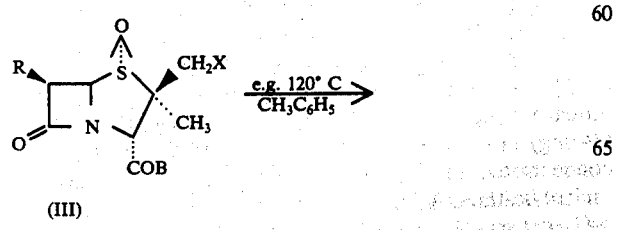

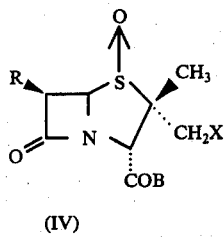

(where COB, R, and X are defined above).

Since both of Compounds (III) and (IV) produce same objective compounds (I) under the same reaction condition, they are equally available as starting materials of this process.

The reaction is carried out by merely heating Compounds (III) or (IV) with a compound of formula HR' (so-called mercapto or sulfenic acid trapping reagent) preferably in nitrogen or argon atmosphere. There is no specific limitation of solvents for the reaction, but more preferable ones are those having no reactive hydrogen (e.g. hydrocarbon-, halohydrocarbon-, ether-, ketone-, amide-, or sulfoxide solvents) when used at 70° to 150° C.

Compounds (II) can be prepared by treating Compounds (I) with a halogenating reagent (particularly halogen e.g. chlorine, bromine, etc.; halide e.g. cupric halides, silver halides), to induce a cyclization according to following reaction scheme:

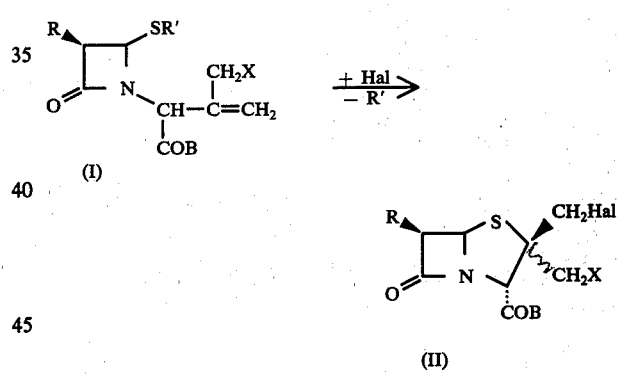

(where COB, Hal, R, R', and X are defined above)

According to an example of suitable methods, halogen is dissolved in an inert organic solvent (e.g. hydrocarbon, halohydrocarbon-, alcohol-, ether-solvents) and is added to a solution of Compound (I), and is let react for 0.5 to 5 hours at −10° C to 50° C to obtain Compounds (II). Amides (e.g. acetamide) can be added for smoother reaction and for surpressing side reactions.

Compounds (II) are useful for preparing cephem compounds (V) by a ring enlargement reaction according to following scheme:

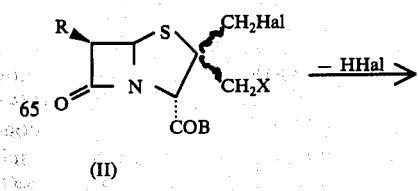

-continued

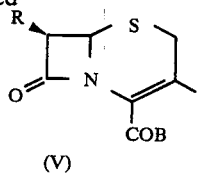

(where COB, Hal, R, and X are defined above).

The reaction is carried out e.g. by heating in a polar (e.g. dimethylsulfoxide) or nonpolar (e.g. toluene) solvent at 40° to 150° C. Some bases also promote the reaction.

Compounds (V) can also be prepared by treating Compounds (I) with a HR'-eliminating reagent (e.g. halogen; organic acid including carboxylic acid, sulfonic acid; inorganic acid including mineral acid; salts of organic bases; alkali metal hydroxide; alkali metal alkoxides; organic bases; boron trifluoride; metal salts of acids; mercuric oxides; cuprous oxide; especially silver fluoride) according to following reaction scheme:

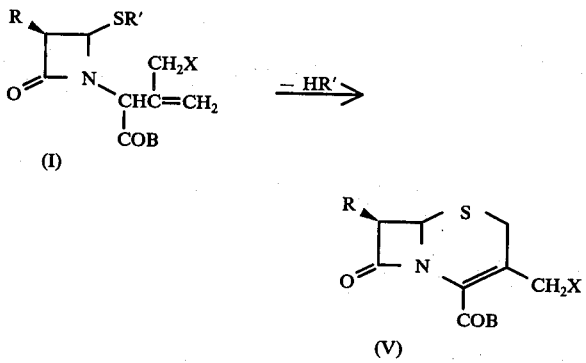

(where COB, R, R', and X are defined above).

The reaction is preferably carried out at 0° to 50° C.

Compounds (I), (II), and (V) can be obtained from above reaction mixtures in conventional manner as extraction, precipitation, recrystallization, chromatography, etc. after removing by-products, excess reagents, solvents, etc. from the reaction mixture.

Compounds (I) and (II) are novel substances showing antibacterial activity and are useful drugs for preventing or treating bacterial infections e.g. caused by Bacillus sp. or Diplococcus sp. in cases of human or animals at a daily dose of e.g. 1 to 5 g per man when administered enterally or parenterally. In forms of carboxy derivatives, they also can be used as intermediates for synthesis of cephalosporins as stated above.

Following examples are given to show the production and use of the Compounds but are not intended to restrict the scope of this invention.

EXAMPLE 1

1. A mixture of diphenylmethyl 6β-phenoxyacetamido-2β-acetoxymethyl-2α-methylpenam-3β-carboxylate-1α-oxide (240 mg) in toluene (15 ml) is refluxed in nitrogen atmosphere for 1 hour. The reaction mixture is concentrated and purified by thin-layer chromatography to give benzhydryl 6-phenoxyacetamido-2β-methyl-2α-acetoxymethylpenam-3α-carboxylate 1β-oxide (220 mg). NMR: $\delta^{CDCl_3}$ 1.64s3H, 1.74s3H, 3.78d(7Hz)1H, 4.28d(7Hz)1H, 4.50s2H, 4.81s1H, 5.18d(2Hz)1H, 6.17dd(2;5Hz)1H.

2. A solution of benzhydryl 6-phenoxyacetamido-2β-acetoxymethyl-2α-methylpenam-3α-carboxylate 1α-oxide (231 mg) and 2-mercaptobenzothiazole (65 mg) in toluene (5 ml) is refluxed in nitrogen atmospher for 1.5 hours, and concentrated to give benzhydryl α-(2-benzothiazolyldithio-3-phenoxyacetamido-4-oxo-azetidin-1-yl)-α-(1-acetoxy-2-propen-2-yl)acetate (277 mg). NMR: $\delta^{CDCl_3}$ 1.98s3H, 4.58s2H, 4.80s2H.

Similarly, a mixture of benzhydryl 6-phenoxyacetamido-2α-acetoxymethyl-2β-methylpenam-3α-carboxylate 1β-oxide (220 mg) and 2-mercaptobenzothiazole (65 mg) in toluene (7 ml) is refluxed for 2.5 hours to give the same product (280 mg).

3. To a solution of benzhydryl α-(2-benzothiazolyldithio-3-phenoxyacetamido-4-oxoazetidin-1-yl)-α-(1-acetoxy-2-propen-2-yl) acetate (280 mg) in methylene chloride (6 ml) is added acetamide (100 mg), and the mixture is stirred at room temperature. Bromine in carbon tetrachloride (1 mmole/ml; 0.2 ml) is added thereto and stirred for an additional hour. The reaction mixture is diluted with methylene chloride, washed with water, dried, and evaporated to give benzhydryl 6-phenoxyacetamido-2β-bromomethyl-2α-acetoxymethylpenam-3α-carboxylate (139 mg) and the starting material (36 mg). IR: $\nu_{max}^{CHCl_3}$ 1790, 1750, 1695 cm$^{-1}$. NMR: $\delta^{CDCl_3}$ 2.87s3H, 3.40d(5.5Hz)1H, 3.61d(5.5Hz)1H, 4.10d(6Hz)1H, 4.45d(6Hz)1H, 4.58s2H, 5.18s1H.

4. To a solution of benzhydryl α-(2-benzothiazolyldithio-3-phenoxyacetamido-4-oxoazetidin-1-yl)-α-(1-acetoxy-2-propen-2-yl)acetate (103 mg) in acetonitrile (5 ml) is added silver fluoride (52 mg) and the mixture is stirred in nitrogen atmosphere for 2.5 hours at room temperature. The reaction mixture is diluted with ethyl acetate, and evaporated after filtering off the insoluble material. The residue is chromatographed on 10% water-silica gel (1.5 g) to give benzhydryl 7-phenoxyacetamidocephalosporanate (35 mg). Yield: 43%.

5. A solution of benzhydryl 6-phenoxyacetamido-2β-bromomethyl-2α-acetoxymethylpenam-3α-carboxylate (5.2 g) in dimethylsulfoxide (25 ml) is kept at 100° C in nitrogen atmosphere for 1 hour. The reaction mixture is diluted with ethyl acetate, washed with brine, dried, and concentrated. The residue (4.4 g) is chromatographed on 10% water-silica gel (130 g) to give benzhydryl 7-phenoxyacetamidocephalosporanate (1.10 g). IR: $\nu_{max}^{CHCl_3}$ 1790, 1735, 1695 cm$^{-1}$. NMR: $\delta^{CDCl_3}$ 2.00s3H, 3.30d(9Hz)1H, 3.65d(9Hz)1H, 4.60s2H, 4.80d(7Hz)1H, 5.10d(7Hz)1H, 5.05d(2.5Hz)1H, 5.98dd(2.5;5Hz)1H.

EXAMPLE 2

1. A mixture of 2,2,2-trichloroethyl 6-phenylacetamido-β-acetoxymethyl-2α-methylpenam-3α-carboxylate 1α-oxide (3.15 g) in toluene (150 ml) is refluxed for 1 hour, and the solvent evaporated. The residue is recrystallized from ether to give 2,2,2-trichloroethyl 6-phenylacetamido-2β-methyl-2α-acetoxymethylpenam-3α-carboxylate 1β-oxide (1.82 g). NMR: $\delta^{CDCl_3}$ 1.65s3H, 2.00s3H, 3.52s2H, 3.98d(6.5Hz)1H, 4.54d(6.5Hz) 1H, 4.55d(6Hz)1H, 4.84d(6Hz)1H, 5.12d(2Hz)1H, 6.02dd(2;5Hz)1H.

2. A mixture of 2,2,2-trichloroethyl 6-phenylacetamido-2β-methyl-2α-acetoxymethylpenam-3α-carboxylate 1β-oxide and 2-mercaptobenzothiazole (34 mg) in toluene (6 ml) is refluxed for 3 hours and concentrated to give 2,2,2-trichloroethyl α-(2-benzothiazolyldithio-3-phenylacetamido-4-oxoazetidin-1-yl)-α-(1-acetoxy-2-propen 2-yl)acetate (140 mg).

IR: $\nu_{max}^{CHCl_3}$ 1680, 1750-1780 cm⁻. NMR: $\delta^{CDCl_3}$ 2.01s3H, 3.70s2H, 4.80s2H.

3. To a solution of 2,2,2-trichloroethyl α-(2-benzothiazolyldithio-3-phenylacetamido-4-oxoazetidin-1-yl)-α-(1-acetoxy-2-propen-2-yl)acetate (140 mg) in methylene chloride (3 ml) is added acetamide (55 mg). Bromine in carbon tetrachloride (1 mmole/ml; 0.12 ml) is added to the stirred mixture at room temperature, and stirring continued for 1 hour. After filtering off insoluble material, the mixture is diluted with methylene chloride, washed with water, dried, and concentrated to give 2,2,2-trichloroethyl 6-phenylacetamido-2β-bromomethyl-2α-acetoxymethylpenam-3α-carboxylate (45 mg). IR: $\nu_{max}^{CHCl_3}$ 1790, 1755, 1680 cm⁻. NMR: $\delta^{CDCl_3}$ 2.10s3H, 3.30d(6Hz)1H, 3.50d(6Hz)1H, 3.60s2H, 4.30d(6Hz)1H, 4.63d(6Hz)1H, 4.73s2H, 5.15s1H.

4. A solution of 2,2,2-trichloroethyl 6-phenylacetamido-2β-bromomethyl-2α-acetoxymethylpenam-3α-carboxylate (45 mg) in dimethylsulfoxide is heated at 100° C in nitrogen atmosphere for 2 hours. The reaction mixture is extracted with ethyl acetate, washed with water, dried, and concentrated. The residue is purified by thin-layer chromatography to give 2,2,2-trichloroethyl 7-phenylacetamidocephalosporanate (14 mg). IR: $\nu_{max}^{CHCl_3}$ 1784, 1745, 1685 cm⁻¹. NMR: $\delta^{CDCl_3}$ 2.10s3H, 3.10d(9Hz)1H, 3.28s2H, 3.43d(9Hz)1H, 5.70dd (2.5;4.5Hz)1H, 5.2–4.5m5H.

EXAMPLE 3

1. A mixture of benzyl 6-phenoxyacetamido-2β-acetoxymethyl-2α-methylpenam-3α-carboxylate 1α-oxide (1.51 g) and 2-mercaptobenzothiazole (0.495 g) in toluene (50 ml) is refluxed for 2.5 hours in nitrogen atmosphere and concentrated to give benzyl α-(2-benzothiazolyldithio-3-phenoxyacetamido-4-oxoazetidin-1-yl)-α-(1-acetoxy-2-propen-2yl)acetate (1.95 g). IR: $\nu_{max}^{CHCl_3}$ 1785, 1745, 1695 cm⁻¹. NMR: $\delta^{CDCl_3}$ 2.00s3H, 4.60s2H, 4.75s2H, 5.75s2H.

2. To a solution of benzyl α-(2-benzothiazolyldithio-3-phenoxyacetamido-4-oxoazetidin-1-yl)-α-(1-acetoxy-2-propen-2-yl)-acetate (1.95 g) in methylene chloride (40 ml) is added acetamide (0.6 g). Bromine in carbon tetrachloride (1 mmole/ml; 2.1 ml) is added to the stirred mixture, and stirring continued for 90 minutes at room temperature. The reaction mixture is filtered, and the filtrate washed with water, dried, and concentrated. The ether soluble part of the residue gives benzyl 6-phenoxyacetamido-2α-acetoxymethyl-2β-bromomethylpenam-3α-carboxylate (1.84 g). Foam. IR: $\nu_{max}^{CHCl_3}$ 1785, 1750, 1690 cm⁻¹. NMR: $\delta^{CDCl_3}$ 2.00s3H, 3.60s2H, 4.20d(5.5Hz)1H, 4.60d(5.5Hz)1H, 4.60s2H, 5.20s2H.

3. A solution of benzyl 6-phenoxyacetamido-2β-bromomethyl-2α-acetoxymethylpenam-3α-carboxylate (1.84 g) in dimethylsulfoxide (10 ml) is heated at 100° C in nitrogen atmosphere for 1 hour. The reaction mixture is diluted with ethyl acetate, washed with water, dried, and concentrated. The residue (1.54 g) is chromatographed on 10% water-silica gel (40g) to give benzyl 7-phenoxyacetamidocephalosporanate (0.3 g). IR: $\nu_{max}^{CHCl_3}$ 1790, 1735, 1695 cm⁻¹. NMR: $\delta^{CDCl_3}$ 2.01s3H, 3.23d(9Hz)1H, 3.60d(9Hz)1H, 4.50s2H, 4.70d(7Hz) 1H, 4.90d(2.5Hz)1H, 5.02d(7Hz)1H, 5.23s2H, 5.80dd(2.5;5Hz)1H.

EXAMPLE 4

1. A solution of benzhydryl 6-phenoxyacetamido-2β-chloromethyl-2α-methylpenam-3α-carboxylate 1α-oxide and 2-mercaptobenzothiazole (141 mg) in toluene (25 ml) is refluxed for 1 hour. The reaction mixture is washed with water, dried, and concentrated to give benzhydryl α-(2-benzothiazolyldithio-3-phenoxyacetamido-4-oxo-azetidin-1-yl)-α-(1-chloro-2-propen-2-yl)acetate (619 mg). IR: $\nu_{max}^{CHCl_3}$ 3410, 1785, 1750, 1695, 1600, 1495 cm⁻¹. NMR: $\delta^{CDCl_3}$ 4.3d(3Hz)2H, 4.6s2H, 5.0–5.8m5H, 6.8–8.0m-H.

2. Acetamide (150 mg) and 1 M bromine in carbon tetrachloride (0.96 ml) is added to a solution of the product (619 mg) prepared by the method of Example 4-(1) dissolved in methylene chloride (10 ml), and the mixture stirred for 50 minutes with ice-cooling. The separated crystal is filtered off, and the filtrate washed with aqueous sodium hydrogen carbonate solution, dried, and concentrated. The residue (640 mg) is chromatographed on 10% water-silica gel (20 g) to give benzhydryl 6-phenoxyacetamido-2β-bromomethyl-2α-chloromethylpenam-3α-carboxylate (380 mg). NMR: $\delta^{CDCl_3}$ 3.2–4.4m4H, 4.55s2H, 5.2s1H, 5.4–5.8m2H, 6.8–7.6m-H.

EXAMPLE 5

The following compounds are prepared in accordance with the procedures described in Examples 1 to 4.

1. p-methoxybenzyl 6-(tetrazol-1-yl)acetamido-2α-chloromethyl-2β-bromomethylpenam-3α-carboxylate from p-methoxybenzyl 6-(tetrazol-1-yl)acetamido-2β-chloromethyl-2α-methylpenam-3β-carboxylate 1α-oxide via p-methoxybenzyl α-(2-benzothiazolhlthio-3-tetrazolacetamido-4-oxoazetidin-1-yl)-α-(1-chloro-2-propen-2-yl)acetate;

2. diphenylmethyl 6-(N-phenylacetylacetamido)-2α-acetoxymethyl-2β-bromomethylpenam-3α-carboxylate from diphenylmethyl 6-(N-phenyl acetylacetamido)-2α-acetoxymethyl-2α-methylpenam-3α-carboxylate 1α-oxide via diphenylmethyl α-[2-benzothiazolyldithio-3-(N-phenylacetylacetamido)-4-oxoazetidin-1-yl]-α-(1-acetoxy-2-propen-2-yl)-acetate; and 3. 6-(2-thienyl)acetamido-2α-(5-methyl-1,3,4-thiadiazol-2-yl)-thiomethyl-2β-chloromethylpenam-3α-carboxylic acid from 6-(2-thienyl)acetamido-2α-(5-methyl-1,3,4-thiadiazol-2-yl)thiomethyl-2β-methylpenam-3α-carboxylic acid 1β-oxide via α-[2-(benzothiazol-2-yl)dithio-3-(2-thienyl)acetamido-4-oxoazetidin-1-yl]-α-[1-(5-methyl-1,3,4-thiadiazol-2yl)thiomethyl-2-propen-2-yl]-acetic acid.

What we claim is:

1. A compound represented by the formula:

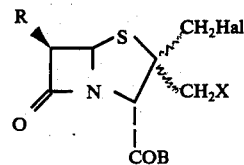

wherein

1. COB = benzhydryloxycarbonyl, Hal = bromo, R = phenoxyacetamido, and X = acetoxy;
2. COB = 2,2,2-trichloroethoxycarbonyl, Hal = bromo, R = phenylacetamido, and X = acetoxy;
3. COB = benzyloxycarbonyl, Hal = bromo, R = phenoxyacetamido, and X = acetoxy;
4. COB = benzhydryloxycarbonyl, Hal = bromo, R = phenoxyacetamido, and X = chloro;

5. COB = p-methoxybenzyloxycarbonyl, Hal = bromo, R = 1-tetrazolacetamido, and X = chloro;
6. COB = diphenylmethoxycarbonyl, Hal = bromo, R = N-phenylacetyl-N-acetylamino, and X = acetoxy; or
7. COB = carboxy, Hal 32 chloro, R = 2-thienylacetamido, and X = 5-methyl-1,3,4-thiadiazol-2-ylthio.